United States Patent
Neame et al.

[11] Patent Number: 5,871,012
[45] Date of Patent: Feb. 16, 1999

[54] LARYNGEAL MASK AIRWAYS AND THEIR MANUFACTURE

[75] Inventors: Simon Neame, Broadstairs; Eric Pagan, Hythe, both of England

[73] Assignee: Smiths Industries PLC, London, England

[21] Appl. No.: 925,668

[22] Filed: Sep. 9, 1997

[30] Foreign Application Priority Data

Oct. 3, 1996 [GB] United Kingdom ................. 9620609

[51] Int. Cl.$^6$ .................................................. A61M 16/00
[52] U.S. Cl. ............................ 128/207.15; 128/201.26; 128/911; 128/207.14
[58] Field of Search .................. 128/207.15, 207.14, 128/200.26, 201.26, 911, 912, DIG. 26; 804/96, 103

[56] References Cited

U.S. PATENT DOCUMENTS

| | | | |
|---|---|---|---|
| 5,297,547 | 3/1994 | Brain | 128/207.15 |
| 5,305,743 | 4/1994 | Brain | 128/207.15 |
| 5,391,248 | 2/1995 | Brain | 128/207.15 |
| 5,743,258 | 4/1998 | Sato et al. | 128/207.15 |

FOREIGN PATENT DOCUMENTS

97/12640   4/1997   WIPO .

*Primary Examiner*—John G. Weiss
*Assistant Examiner*—V. Srivastava
*Attorney, Agent, or Firm*—Pollock, Vande Sande & Amernick

[57] ABSTRACT

A laryngeal mask assembly has a mask portion formed by a flexible bag enclosing a mount attached to the patient end of a tube. The bag is sealed to the mount around an opening at the patient end of the tube. The neck of the bag is sealed to the tube rearwardly of an opening from a inflation lumen by which the bag can be inflated to form a cushion on the forward surface of the mount. The mount is curved rearwardly around its outer edge and the bag also inflates away from the rear surface of the mount to provide an expandable cushion on the rear of the mount.

7 Claims, 2 Drawing Sheets

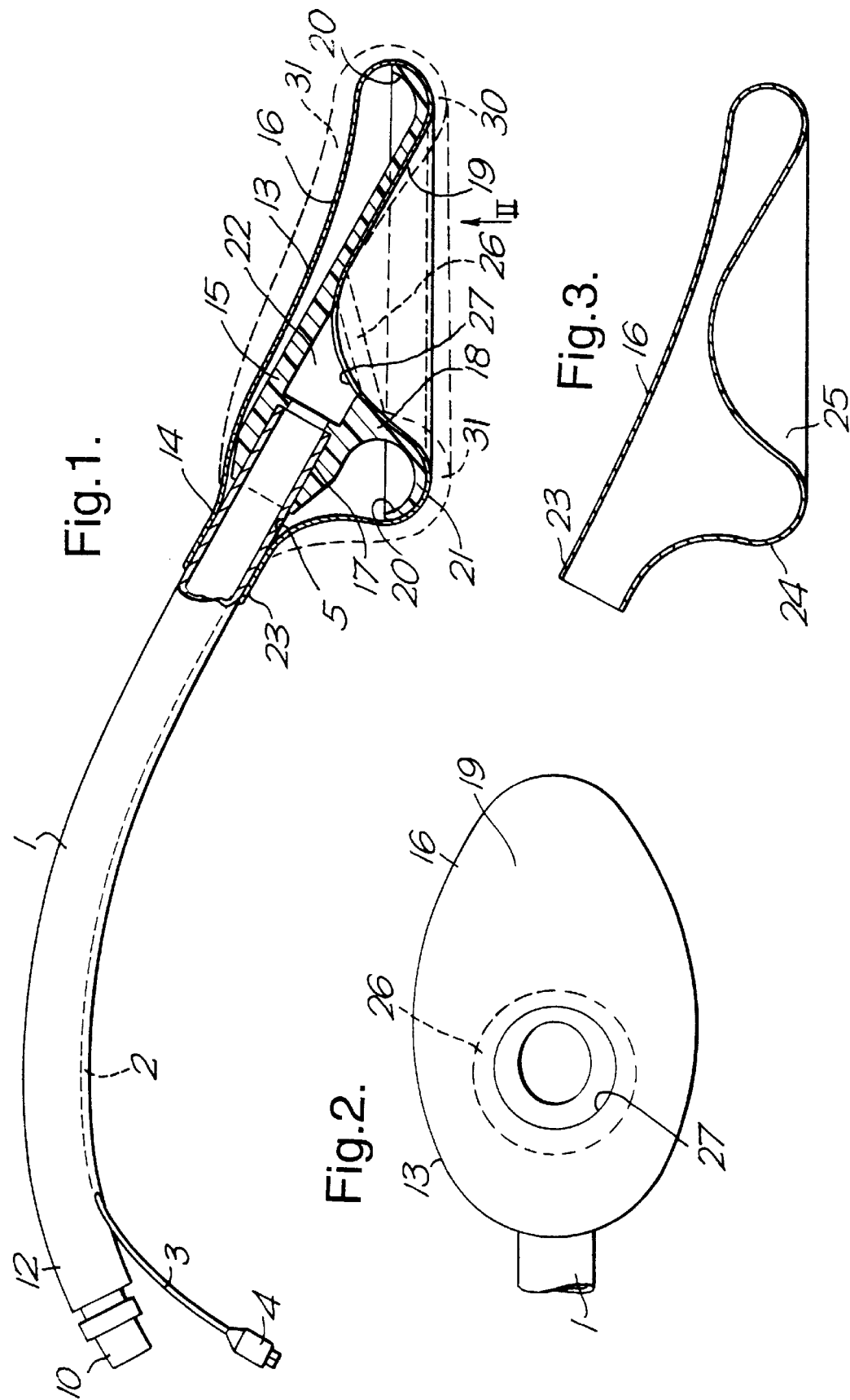

LARYNGEAL MASK AIRWAYS AND THEIR MANUFACTURE

CROSS REFERENCE TO RELATED APPLICATIONS

The subject matter of the present invention is related to the inventions described in Neame et al., U.S. application Ser. No. 08/956,358, filed Oct. 23, 1997 for "Laryngeal Mask Airways and their Manufacture", and Neame, U.S. application Ser. No. 08/961,038, filed Oct. 30, 1997 for "Laryngeal Mask Airways and their Manufacture".

BACKGROUND OF THE INVENTION

This invention relates to laryngeal mask airways and their manufacture.

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. Nos. 5,355,879, 5,305,743, 5,297,547, 5,282,464, GB 2267034, U.S. Pat. Nos. 5,249,571, 5,241,956, 5,303,697, GB 2249959, GB 2111394, EP 448878, U.S. Pat. No. 4,995,388, GB 2205499, GB 2128561 and GB 2298797.

Laryngeal masks have several advantages over endotracheal tubes, which are longer and seal with the trachea below the vocal folds. It can be difficult, however, to manufacture the patient end of the mask at low cost.

BRIEF SUMMARY OF THE INVENTION

It is an object of the present invention to provide an improved laryngeal mask assembly and method of manufacture.

According to one aspect of the present invention there is provided a laryngeal mask assembly including a mask portion and an elongate tube with an inflation lumen extending along its length, the mask portion being adapted during use to locate in the hypopharynx and to open on its forward side to the patient's airway, wherein the mask portion includes a mount member attached with the patient end of the tube, the mount member being generally elliptical and having a forward surface and a rear surface, the tube opening at the forward, patient end of the assembly via an opening on the forward surface of the mount member, the mask portion including a flexible bag member encompassing said mount member, the bag member being sealed with the mount member around the opening on the forward surface and being sealed at its neck towards the patient end of said assembly such that the inflation lumen opens into the bag member and such that the bag member provides an expandable cushion on the forward surface of the mount member.

Preferably, the bag member is arranged also to provide an expandable cushion on the rear surface of the mount member. The bag member preferably has a forward portion conforming generally to the shape of the patient end of the mount member. The mount member may have an outer edge curved rearwardly. The neck of the bag member may be attached to the tube.

According to another aspect of the present invention there is provided a method of manufacture of a laryngeal mask assembly including the steps of providing a mount member of generally elliptical shape at the patient end of a tube, the tube having an inflation line extending along its length and opening towards the patient end of the assembly, providing a bag member, inserting said mount member into said bag member, sealing the neck of said bag member with the assembly to the rear of the patient end opening of the inflation lumen, and sealing the bag member to the forward end of said mount member such that the bag member can expand away from the mount member to provide a cushion on the forward surface of the mount member.

According to a further aspect of the invention there is provided a laryngeal mask assembly made by a method according to the above other aspect of the invention.

A laryngeal mask assembly according to the present invention, will now be described, by way of example, with reference to the accompanying drawings.

BRIEF DESCRIPTION OF THE DRAWINGS

FIG. 1 is a side elevation view of the assembly;

FIG. 2 is a view of the forward end of the assembly along the arrow II of FIG. 1;

FIG. 3 is a side elevation view of the bag; and

DETAILED DESCRIPTION OF THE PREFERRED EMBODIMENT

Figure 4:
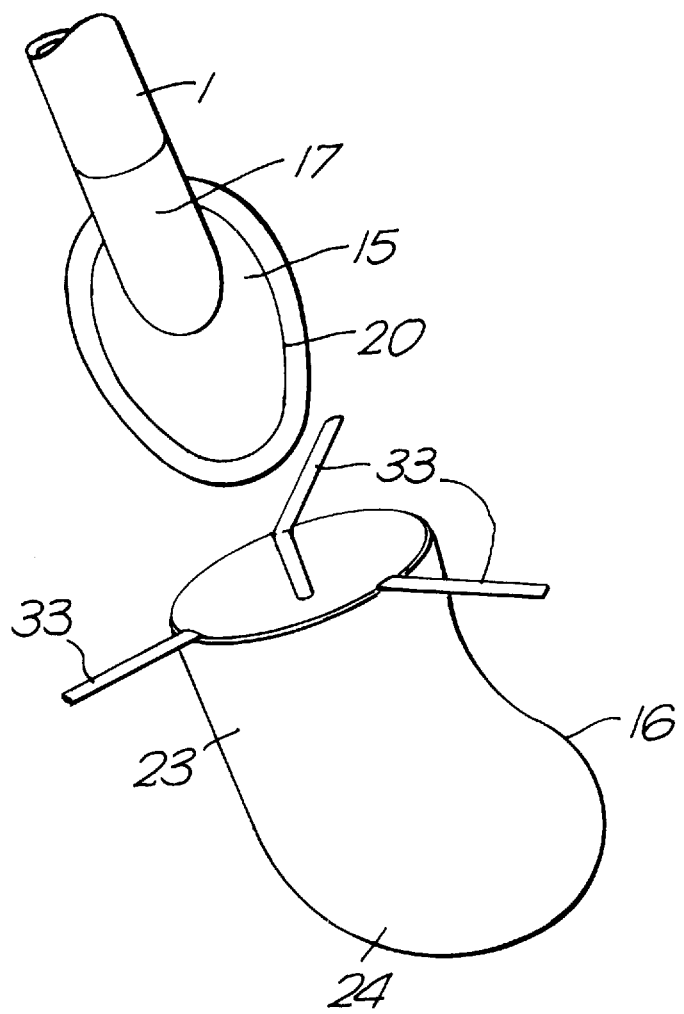
FIG. 4 illustrates a step in the manufacture of the assembly.

With reference to FIGS. 1 and 2, the assembly comprises a bendable tube 1 of a plastics material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 opens into the mask portion 13, through a hole 5 formed in the outside of the tube 1.

The mask portion 13 comprises a mount member 15 and a flexible bag member 16. The mount member 15 is moulded from a bendable plastics material, such as PVC, and has a hollow cylindrical sleeve 17 at its rear end, in which the forward, patient end 14 of the tube 1 is inserted and joined. The forward, patient end 18 of the mount member 15 is of an inverted dish shape, with a generally elliptical or egg-shape outline and with a concave recess 19. The peripheral edge 20 of the mount member 15 is curved rearwardly to form a convex peripheral forward surface 21 lying on a flat plane inclined at an angle of about 30° to the axis of the patient end 14 of the tube 1. The mount member 15 has a reduced thickness about its periphery so that the curved edge 20 is resilient. A bore 22 extends forwardly through the mount member 15, as a continuation of the bore through the sleeve 17, and opens into the rear part of the recess 19. Instead of opening through the hole 5, the inflation lumen 2 could communicate with a passage through the mount member 15, which opens on its external surface.

With reference now also to FIG. 3, the bag member 16 is blow moulded from a flexible, resilient plastics material, such as PVC, polyurethane, silicone, EVA, TPE, polyether block amide or the like. The bag 16 has a sock shape with an open ankle or neck portion 23 at its upper, rear end and a lower, forward foot portion 24 with an egg-shape profile having the same general outline as the mount member 15. The lower, forward surface of the foot portion 24 has a concave recess 25 of the same shape as the recess 19 in the mount 15. The bag 16 encompasses the forward end of the assembly, enclosing the entirety of the mount 15, and having its neck 23 attached to the outside of the patient end 14 of the tube 1, just rearwardly of the inflation lumen opening 5. The neck 23 can be attached to the tube 1 by a solvent, adhesive or by welding. In alternative assemblies, the neck 23 of the bag 16 could be attached to the mount itself, providing there was some communication between the inflation lumen 2 and the interior of the bag. The bag 16 is also attached to the concave recess 19 of the mount 15 along an annular band 26 extending around the opening of the bore 22, to seal the bag material to the mount. Alternatively, the bag 16 could be sealed to the inside of the bore 22. The material of the bag 16 within this band 26, overlying the opening of the bore 22 is cut away to form a hole 27 in the bag 16 that provides access to the bore in the mount. The hole 27 could have a series of holes or slits to prevent entry of the epiglottis. The bag 16 provides an inflatable cuff at the forward end of the assembly.

The bag 16 could be attached to the edge surface 20 or to the rear surface of the mount 15. The bag 16 could be of an elastomeric material, such as silicone, injection moulded to produce regions of reduced wall thickness so that the bag expands to a greater extent in these regions. In this way, the bag may be given an inflated shape that complies more closely with the patient's anatomy. The bag could contain a foam material so that it naturally adopts an expanded state and can be deflated by applying suction to the connector.

With reference now also to FIG. 4, the assembly can be manufactured reliably at low cost. The individual components can be easily formed, the tube 1 being extruded, and the mount 15 and bag 16 being moulded in conventional ways suitable for automation. Assembly of the components is also easily achieved. The mount 15 is joined to the patient end 14 of the tube 1 and closes the patient end of the inflation lumen 2. The opening 5 is then cut into the inflation lumen 2 just to the rear of the mount 15. The neck 23 of the bag 16 is stretched by a dilator 33, the mount 15 is inserted into the bag 16 and the neck is allowed to contract about the patient end of the tube 1, just rearwardly of the inflation lumen opening 5. The neck 23 of the bag 16 is then bonded to the outside of the tube 1 in any conventional way. The bag 16 is also sealed to the mount 15 around the opening to the bore 22, in the concave recess 19 on the forward surface. The hole 27 is subsequently cut through the bag material overlying the opening to the bore 22 so that ventilation gas can flow along the length of the assembly.

The assembly is introduced to the patient in the usual way with the cuff deflated and conforming generally to the contours of the mount 15, as shown by the solid lines in FIG. 1. When correctly positioned, a syringe or the like is connected to the connector 4 and a measured volume of air is supplied via the inflation line 3 and lumen 2 to the space between the outer surface of the mount 15 and the inner surface of the bag 16. This causes the bag 16 to inflate and distend away from the mount 15 where it is not attached to it. When fully inflated, the bag 16 takes up the shape shown by the broken lines in FIG. 1. The material of the bag 16 inflates away from the forward surface of the edge 20 of the mount 15 to form an annular conformable cushion 30 around the forward face of the patient end of the assembly. The bag 16 also inflates at the rear of the mount 15 to form a rear cushion 31. The forward cushion 30 provides a seal around the opening of the larynx by conforming to the shape of the anatomy in this region. The rear cushion 31 engages the pharyngeal wall to prevent rearward displacement of the assembly and may also gently urge the forward cushion 30 into sealing engagement.

What we claim is:

1. A laryngeal mask assembly comprising: an elongate tube with an inflation lumen extending along its length; and a mask portion attached with a patient end of said tube, said mask portion during use forming a seal in the hypopharynx, wherein said mask portion includes a mount member of generally elliptical shape and having a forward surface and a rear surface, wherein said tube opens at a forward, patient end of the assembly via an opening on a forward surface of said mount member, wherein said mask portion includes a flexible bag member, said bag member having a forward portion and a neck portion, wherein said bag member encompasses said mount member, and wherein said bag member is sealed with said mount member around said opening on said forward surface and at its neck towards the patient end of said assembly such that said inflation lumen opens into said bag member and such that said bag member provides an expandable cushion on said forward surface of said mount member.

2. An assembly according to claim 1, wherein said bag member also provides an expandable cushion on said rear surface of said mount member.

3. An assembly according to claim 1, wherein said forward portion of said bag member conforms generally to the shape of a forward end of said mount member.

4. An assembly according to claim 1, wherein said mount member has an outer edge curved rearwardly.

5. An assembly according to claim 1, wherein said neck of said bag member is attached to said tube.

6. A laryngeal mask assembly comprising: an elongate tube with an inflation lumen extending along its length, said inflation lumen having an opening towards a patient end of said assembly; and a mask portion attached with a patient end of said tube, said mask portion during use forming a seal in the hypopharynx, wherein said mask portion includes a mount member of generally elliptical shape and having a forward, concave surface and a rear surface, wherein said tube opens at a forward, patient end of the assembly via an opening on a forward surface of said mount member, wherein said mask portion includes a flexible bag member, said bag member conforming generally to the shape of a patient end of said assembly and having a forward portion and a neck, wherein said bag member encompasses said mount member and is sealed to said forward surface of said mount member around said opening, and wherein said neck of said bag member is sealed to said assembly to the rear of said opening of said inflation lumen such that said inflation lumen opens into said bag member and such that said bag member provides an expandable cushion on said forward and rear surfaces of said mount member.

7. A method of manufacture of a laryngeal mask assembly comprising the steps of:
providing a tube with a mount member of generally elliptical shape at a patient end of said tube, said tube having an inflation line extending along its length, said inflation line having an opening towards a patient end of the assembly, and said mount member having a forward end with an opening through which said tube opens at the patient end of the assembly; providing a bag member of a flexible material, said bag member having a forward end and a neck at a rear end; inserting said mount member into said bag member; sealing said neck of said bag member with the assembly to the rear of the patient end opening of said inflation line; and sealing said bag member to said forward end of said mount member such that said bag member can expand away from said mount member to provide a cushion at said forward end of said mount member.

* * * * *